(12) United States Patent
Heigl (10) Patent No.: US 10,039,607 B2
(45) Date of Patent: Aug. 7, 2018

(54) DISPOSABLE AND RADIOLUCENT REFERENCE ARRAY FOR OPTICAL TRACKING

(75) Inventor: Rupert Heigl, Markt Schwaben (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 13/389,772

(22) PCT Filed: Aug. 27, 2009

(86) PCT No.: PCT/EP2009/061084
§ 371 (c)(1),
(2), (4) Date: Feb. 9, 2012

(87) PCT Pub. No.: WO2011/023232
PCT Pub. Date: Mar. 3, 2011

(65) Prior Publication Data
US 2012/0143050 A1    Jun. 7, 2012

(51) Int. Cl.
A61B 34/20    (2016.01)
A61B 17/00    (2006.01)
A61B 90/00    (2016.01)

(52) U.S. Cl.
CPC .............. *A61B 34/20* (2016.02); *A61B 90/39* (2016.02); *A61B 2017/0023* (2013.01); *A61B 2034/2055* (2016.02); *A61B 2090/3983* (2016.02); *Y10T 29/302* (2015.01)

(58) Field of Classification Search
CPC .......... G03B 42/047; G03C 5/16; G03C 5/17; G03C 11/02; A61B 2019/5483; A61B 19/54; A61B 2019/5251; A61B 2017/0023; A61B 2090/3983; A61B 2034/2055; A61B 90/39; A61B 34/20

USPC ................ 600/300, 549, 587, 407; 128/898; 434/267
See application file for complete search history.

(56) References Cited

U.S. PATENT DOCUMENTS

| | | | |
|---|---|---|---|
| 5,123,040 A * | 6/1992 | Fabian .......................... | 378/182 |
| 5,643,268 A | 7/1997 | Vilsmeier et al. | |
| 5,920,741 A * | 7/1999 | Nishimoto .................... | 396/612 |
| 6,226,548 B1 | 5/2001 | Foley et al. | |
| 6,236,875 B1 | 5/2001 | Bucholz et al. | |
| 6,405,072 B1 | 6/2002 | Cosman | |
| 6,412,491 B1 * | 7/2002 | Rusin ............................. | 128/897 |
| 6,490,467 B1 | 12/2002 | Bucholz et al. | |
| 6,738,656 B1 | 5/2004 | Ferre et al. | |
| 6,856,828 B2 | 2/2005 | Cossette et al. | |
| 6,873,867 B2 | 3/2005 | Vilsmeier | |
| 6,893,447 B2 | 5/2005 | Dominguez et al. | |

(Continued)

FOREIGN PATENT DOCUMENTS

WO    99/15097    4/1999

OTHER PUBLICATIONS

International Search Report for International Application No. PCT/EP2009/061084 dated Jun. 1, 2010.

*Primary Examiner* — Elmer Chao
(74) *Attorney, Agent, or Firm* — Tucker Ellis LLP (57) ABSTRACT

A reference foil comprises an unsymmetric marker foil device which advantageously includes spatially separated pieces of a marker material foil in unsymmetric arrangement and/or at least one unsymmetric integral piece of the marker material foil. The reference foil and a carrier device for the same may be used for example in image-guided surgery.

17 Claims, 2 Drawing Sheets

(56) References Cited

U.S. PATENT DOCUMENTS

| | | | |
|---|---|---|---|
| 6,932,823 B2 | 8/2005 | Grimm et al. | |
| 6,993,374 B2 | 1/2006 | Sasso | |
| RE39,133 E | 6/2006 | Clayton et al. | |
| 7,139,601 B2 | 11/2006 | Bucholz et al. | |
| 7,326,212 B2 | 2/2008 | Huebner | |
| 7,477,926 B2 | 1/2009 | McCombs | |
| 2003/0161442 A1 | 8/2003 | Zeiss | |
| 2004/0147839 A1 | 7/2004 | Moctezuma et al. | |
| 2005/0049485 A1 | 3/2005 | Harmon et al. | |
| 2006/0009693 A1* | 1/2006 | Hanover | A61B 5/415 600/407 |
| 2007/0135712 A1* | 6/2007 | Maschke | 600/433 |
| 2008/0317281 A1* | 12/2008 | Goldbach | G06F 19/3412 382/103 |
| 2010/0100081 A1* | 4/2010 | Tuma | A61B 17/00 606/1 |
| 2010/0113912 A1* | 5/2010 | Traboulsi et al. | 600/414 |

\* cited by examiner

DISPOSABLE AND RADIOLUCENT REFERENCE ARRAY FOR OPTICAL TRACKING

This application is a national phase of International Application No. PCT/EP2009/061084 filed Aug. 27, 2009 and published in the English language.

The present invention is directed to a disposable and radiolucent reference array for optical tracking, in particular a reference foil comprising a marker foil device, with features according to the independent claims. The invention also relates to a carrier device for such a reference array and a method for producing the reference array.

Intra-operative navigation (e.g. by using Image-Guided Surgery—IGS) makes use of reference bodies with optical markers in a particular geometry. Reference arrays or reference stars are typical terms for these structures. They frequently display a geometry of up to three markers fixed to a mechanical holding structure and are usually attached to an object such as for example a body part (e.g. a bone structure such as a vertebra or femur) or an instrument (e.g. a scalpel or a catheter) which requires tracking, i.e. ascertaining of its location (e.g. in an absolute coordinate system, i.e. a coordinate system centred in the body part or the instrument) or position (e.g. relative to the patient's body or a different object, described e.g. in a coordinate system relative to the body or the object) during surgery. One distinguishes between passive markers which reflect (infrared) light of an external source and active markers which emit light themselves. There are reasons for using each variant and naturally both variants coexist today. The current invention describes an apparatus which provides a number of advantages over conventional markers.

Passive markers are chosen for their easy handling, since there is no need for having a cable attached to the instruments and all marker can be tracked simultaneously. Active markers are usually triggered and powered subsequently and movement could have an impact on the detection accuracy. Passive markers usually contain a retro-reflective coating which is very sensitive and is not suitable for steam-sterilization. Thus, these markers are recommended to be disposed of after each surgery in order to avoid significant reduction of navigation accuracy. Prior to each surgery, a new set of sterile markers must be fixed to objects which require tracking. Depending on the surgery, there may be up to e.g. 20 markers required. Due to the necessity of precise fixation of the markers this can take a team of medical personnel several minutes. There is a strict time schedule in modern hospitals and additional time-consuming tasks are generally not accepted in such a working environment.

The subject-matter of the appended independent claims solves the above problems by simplifying image-guided surgery while in particular supporting disposability of the reference array.

Advantageous embodiments of the invention are described by the dependent claims. Features of different embodiments may be combined with one another.

The invention advantageously comprises a reference array having the form of a reference foil comprising a marker foil device, wherein the marker foil device is unsymmetric. According to an embodiment of the invention, marker foil device comprises a plurality of markers or consists of these markers. Preferably, the marker foil device is unsymmetric in the meaning that the arrangement (i.e. spatial distribution) of these markers is unsymmetric. The markers may be pieces (e.g. dot-shaped pieces) of a marker material foil as described later. The markers may be symmetric, e.g. may have a circular shape, if there is a plurality of markers.

Within the framework, the term of foil denotes in particular a planar structure of preferably small and preferably homogeneous thickness. The reference foil comprises for example a support foil made of a preferably thin support foil material. The support foil comprises advantageously a plastic material (e.g. Mylar™) with a preferable thickness of less or equal about 1 mm or 2 mm and/or more than 0.05 mm or 0.1 mm, preferably having a thickness of 0.5 mm or about 0.5 mm (e.g. 0.5 mm±0.05 mm). Mylar™ provides the advantage of dissolving under steam sterilisation if it is laminated with PE (polyethylene), preferably a linear low-density polyethylene. This inhibits multiple use of the marker foil after a carrier device carrying the marker foil has been sterilised. Thus, reusing a possibly damaged and/or contaminated marker foil may also be avoided. The support foil may be cut in a square or rectangular format or circular format and thus display the form of a rectangular or circular sheet and/or label. In case of a rectangular format, the corners are advantageously rounded-off in order to avoid damage to the foil when being handled. Advantageously, the supporting foil is flexible such that it may be attached to objects of different geometry and is stress-resistant and/or strain-resistant in order to avoid a change in geometry due to mechanical and/or thermal influences such as damage due to touching and/or thermal expansion. To this end, the support foil preferably has low values for the coefficients of elasticity and/or thermal expansion. The support foil may comprise only one or more, i.e. multiple layers of material.

In accordance with the invention, the reference foil also comprises a marker foil device which includes at least one, preferably at least two or more, more preferably three markers. Advantageously, the markers are attached to the support foil to form a marker foil device. The function of a marker is to be detected by a marker detection device (for example, a camera—in particular a camera sensitive to infrared radiation—or an ultrasound receiver), such that its spatial position (i.e. its spatial location and/or alignment) can be ascertained. Such markers can be active markers. An active marker emits for example electromagnetic radiation and/or waves, wherein said radiation can be in the infrared and/or visible and/or ultraviolet spectral range. To this end, an active marker may comprise an emitting material such as a luminescent, especially chemoluminescent and/or photoluminescent (i.e. fluorescent and/or phosphorescent) material. The marker can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. Conventionally, a marker preferably has a spherical and/or spheroid shape and may therefore be referred to as a marker sphere; markers can also, however, exhibit a cornered—for example, cube-shaped—shape. In accordance with an embodiment of the invention, the markers may have the form of a thin foil (in the following also referred to as a marker material foil) comprising a plastic material which is able to fulfil the physical characteristics of a marker as defined above. The marker material foil may have a thickness of 0.5 mm or about 0.5 mm (e.g. 0.5 mm±0.05 mm). The thickness of the marker material foil is preferably larger than 0.1 mm or 0.05 mm and/or smaller than 2 mm or 1 mm. A total thickness of marker material foil and support foil if attached to each other (i.e. of the reference foil) may therefore amount to between about 0.09 mm and about preferably 2 mm.

Preferably, the marker foil device comprises a marker material foil or is constituted of a marker material foil. The marker foil device may comprise a plurality of (discrete) pieces of such a marker material foil or may be constituted thereof. In particular, the arrangement of the plurality of pieces is unsymmetric, while the (shape or appearance of the) individual pieces may be symmetric. In particular, the pieces of marker material foil respectively represent one marker. However, the marker foil device may comprise one single (integral) piece of marker material foil only. In particular, the (shape or appearance of the) single piece is unsymmetric, if there is only one single piece. The pieces of marker material foil may be mechanically separated, for instance cut and/or punched for instance in a circular or rectangular (in particular quadratic) form out of a bulk (e.g. sheet or ribbon) of a marker material foil. The pieces respectively display physical characteristics (in particular reflectance and/or emission characteristics) of markers. The marker material foil may also be referred to as a retroreflecting foil. The marker material foil and the support foil advantageously have comparable mechanical properties such as elasticity and thermal expansion in order to ensure a preferably fixed and stable geometric relationship between the markers and the support foil after fixing the markers to the support foil. Such a relationship may also be supported if the reference foil is flexed (especially formed into a curved surface) after fixing the marker foil device to the support foil. The marker foil device is preferably attached to the support foil as a kind of label. As may be deduced from the above the marker foil device has in particular a planar structure, in particular a two-dimensional appearance.

According to an embodiment of the invention, a single piece of marker material foil may comprise a multitude of parts. These parts are preferably constituted to be distinguishable by a detection device so that each part may act as an individual marker, when detected by the detection device of a navigation system. To this end, the marker material foil may be interspersed with conventional (in particular plastic) material which does not have marker characteristics (within the framework of this invention also referred to as non-marker material). A marker foil device may also consist of a single piece of marker foil. This marker foil may have a shape which displays the unsymmetric geometric pattern without being interspersed with non-marker material. In particular, the prominent parts of the geometric pattern, like edges and/or recesses and/or projections may be identified as individual markers by the detection device. Thus, these prominent parts may act like individual markers when detected by the detection device of the navigation system. The marker foil device may comprise one or more integral unsymmetric pieces of marker material foil. As mentioned above, it is also possible to construct a marker foil device from a number of discrete and/or disjunct pieces of marker material foil (i.e. in particular spatially separate, i.e. discrete, markers) which are not directly physically and/or mechanically connected to one another (by other parts of marker material foil) and advantageously form the unsymmetric geometric pattern when used in the reference array. In particular, the marker foil device is not constituted by one single body of circular shape since the appearance of such a marker would be equal for different viewing directions and identical viewing angle with respect to a line normal to the marker.

The markers (e.g. pieces of marker material foil) may be attached to the surface of the support foil and/or inserted into recesses and/or cut-outs of the support foil. A fixed mechanical connection of the marker foil device to the support foil may be achieved by a bonded connection or material-locking, respectively. Advantageously, such a connection is achieved by gluing.

The reference foil, i.e. both the support foil and the markers, may be coated with a protective layer which advantageously comprises nanoparticles in order to make the reference foil less susceptible to contamination such as by fluids dispersed during an operation and adhering to the surface of the reference foil. Alternatively, only the marker foil may be coated with such a protective layer, the support foil remaining uncoated. The process of coating may be performed by any known technique such as physical/chemical vapour deposition (PVD, CVD) or by coating the surface with self-assembled monolayers (SAMs) in solution.

As mentioned above, the marker foil device is unsymmetric. This is at least the case if the reference foil is attached to the carrier device. The term "unsymmetric" means in particular that the marker foil device does not display any symmetry and/or that the appearance of the marker foil device depends on the angle of view and/or direction of view. In particular, the appearance of the marker foil device is different for identical angle of view but different directions of view. The direction of view may be characterised by the azimuth (i.e. azimuthal angle) between a (straight) line connecting the position of the detection device and the position of the marker foil device and a reference (in particular, a baseline) direction. This is preferably the case for all directions of view or at least for the major part of possible directions of view. This major part is preferably contiguous, i.e. continuous. In particular, for (any) particular angle of view, there is no direction of view for which the appearance is identical. In particular, the marker foil device does not show a periodic reappearance of geometric features, like the four corners of a square. In particular, the marker foil device may form a shape by a simple piece of marker foil or by the arrangement of the plurality of markers. In particular this shape displays a geometric pattern (which is in particular two-dimensional) on the surface of the support foil or within the reference foil, respectively. This geometric pattern, in two dimensions, advantageously three dimensions, does not display any symmetry in particular when viewed from the location of the detection device and/or by the detection device and/or in the viewing direction from the location of the detection device. Especially when the reference foil is fitted to a carrier device for carrying the reference foil, the appearance of the geometric pattern of the marker foil device from the point of view of the detection device (in particular, when projected into a two-dimensional viewing plane of the detection device) is advantageously such that it is non-symmetric. Preferably, the geometric pattern lacks symmetry in any case (especially from any viewing direction which permits detection of the marker foil device by the detection device). In particular the lack of symmetry becomes apparent when the marker foil device is viewed at an angle of incidence with respect to the surface of the support foil to which the marker foil device is attached of preferably less than 90°, more preferably less than 80°. Advantageously, the lack of symmetry exists at least if the marker foil device is viewed in a direction which is not tangential and/or parallel to that surface of the support foil. In accordance with the invention it is however advantageous that the marker foil device is unsymmetric in the sense that the geometric pattern lacks symmetry at least from the perspective of the detection device. That is, the solid angle within which the marker foil device does not show any symmetry and/or changes its appearance is larger than $0.2\pi$ or $0.5\pi$ or $\pi$ or $2\pi$ and/or may be smaller than or equal to $2\pi$ or $3\pi$ or $4\pi$. Thereby, a unique determination of the position of the reference foil with respect to e.g. the location of the detection device or any other suitable object and/or identification of the particular reference foil may be carried out. The aim is to have no more than one reference foil simultaneously in use which, when viewed by the detection device, displays the same geometric appearance. To this end, the geometric pattern displayed by the marker foil device on the reference foil preferably lacks planar symmetry (e.g. if the reference foil is placed flat on a plane). This will ensure that also if the reference foil is flexed in three dimensions (e.g. if it is formed around a carrier device), no symmetry of the marker foil device appears from the viewpoint of a detection device used for detecting the marker foil device. Consequently, each reference foil used during an operation may display a marker foil device pattern (i.e. a geometric pattern of the marker foil device) which is different from the one of any other reference foil used simultaneously (e.g. during the same surgical operation), i.e. each reference foil may display a unique marker foil device pattern. The geometric pattern may be created by the shape of a single piece of marker and/or by the arrangement of a plurality of markers on the reference foil. For example, four discrete markers (e.g. four discrete pieces of marker material foil) may be attached to the support foil in a random and/or non-symmetric pattern. Alternatively or additionally, at least one integral marker may be used, the shape (geometric pattern) of which lacks symmetry in three dimensions (e.g. when fixed to a carrier device and viewed from the viewpoint of a detection device) or at least in two dimensions (e.g. when attached to the support foil held in a plane formed by the support foil).

The reference foil, in particular the support foil advantageously has at least one attaching part for attaching the reference foil to a carrier device. Such an attaching part may comprise a cut-out or punch-out which may be slid over or fits over a prominent feature such as a tooth of a carrier device. Additionally or alternatively, the attaching part may comprise a part of foil, in particular a part of foil appended to e.g. an edge of the support foil (preferably a part of the support foil), which part is gripped by a fixing part of the carrier device such as a clamp or clip, especially a spring clip.

The reference foil may have sheet-like form, in particular sheet form. A sheet form denotes in this context a planar geometry of the reference foil into which the reference foil may be brought without flexing it. Having a sheet form, the reference foil may be fixed to a frame-like or planar carrier device. However, a reference foil in sheet form may also be attached to (in particular wrapped around and/or stuck to) a carrier device of other geometry. Alternatively, the reference foil may have at least partly tubular form or be formed at least partly as a hollow cone such that it may be attached to or slid over a carrier device having conical or cylindrical geometry.

As another part of the invention, a carrier device for carrying the reference foil during an operation or other application, in particular medical application is described. The carrier device may be formed as an inflexible support frame. In particular the support frame is constituted such that the reference foil may be spanned into an opening, especially a centre opening, of the support frame. In that case, the reference foil preferably displays sheet-like geometry. The frame may have polyangular (e.g. rectangular), in particular quadratic, and/or round (e.g. circular or elliptical) shape. In particular, the geometry of the outer rim of the support frame is adapted to or fits the geometry of the reference foil, respectively. Alternatively, the carrier device may have at least partly conical or at least partly cylindrical form. In that case, the reference foil may have at least partly hollow-conical or at least partly tubular geometry, respectively. The carrier device may also be adapted to carry reference foils of different (in particular planar) geometries and/or sizes.

The carrier device advantageously has at least one fixing part for preferably detachably fixing the reference foil such that its position with respect to the carrier device is secured at least during use. The fixing part may be designed for engaging into or with the attaching part of the reference foil and thus have properties as described above in the context of the attaching part. Further, the fixing part may have the form of a rectangular and/or angled prominent feature such that a single fixing part may suffice for uniquely fixing the reference foil such as to give the reference foil a stable position on the carrier device in particular by inhibiting a movement of the reference foil in a direction lateral to the prominent feature. The fixing parts support a stable and known position of the reference foil to the carrier device when the reference foil is attached to the carrier device. According to an embodiment of the invention, at least a subset out of the set of fixing parts may be movable with respect to the carrier device, e.g. located on a tensioning part which may comprise a double plate which is attached to the carrier device slidably over a part of the carrier device. The tensioning part may thus have the form of a sledge sliding over a surface of the support frame. After the reference foil has been attached to the carrier device, such a plate may then be slid into an outward direction of the carrier device (i.e. preferably away from its geometric centre) such that a certain tension is applied to the reference foil in order to avoid hollow spaces between the reference foil and the support frame. The fixing parts may therefore also fulfil the purpose of alignment parts which support a certain, in particular fixed, alignment of the reference foil on the support frame.

According to a preferred embodiment of the invention, the carrier device comprises a material which is transparent for X-rays (a so-called radiolucent material) such that it does not appear on images produced by X-rays e.g. when the carrier device is in use. To this end, the carrier device may at least partly be produced of a plastic such as poly(etheretherketone) (PEEK), poly(etherketoneketone) (PEKK), polyetherimide (PEI), polyethylene therephthalate (PET), polypropylene (PP) or any other polyethylene compound.

The carrier device advantageously is coupled to a holding part which may be used for attaching the carrier device to an object which is to be tracked during IGS such as a body part or an instrument. The holding part may comprise an elongated shaft and a hollow screw thread on the elongated shaft and/or a clamp and/or a screw.

Advantageously, the carrier device comprises at least one curved, in particular bent surface onto which the reference foil is attached. This has the effect that the reference foil undergoes a slight force (in particular a tightening force) when fixed to the carrier device. In this was, in particular, the generation of hollow spaces between the surface of the carrier device and the reference foil during the attaching process may be avoided. Thus, achieving a well-defined position of the marker foil device relative to the carrier device (and, in the end, to the object to which the carrier device is coupled) is ensured. The larger the curvature of the curved surface is, the better usually the fixation of the reference foil will be. However, surfaces made of marker material foil may be recognized and/or detected, respectively, by a detection device only in a viewing direction with about +/−60° angle of incidence onto the marker surface. Thus, the curvature of the curved surface is advantageously limited to a value such that the characteristic marker pattern on the reference foil may still be detected by the detecting device from its point of view. If, for example, three or more markers are used for forming the marker foil device, there will be a kind of umbra or deepest shadow (which is created by overlapping spatial angles of visibility to a detection device), within which all three marker foil devices will despite the curvature of the curved surface be simultaneously detected from the viewpoint of the detecting device. The markers have to be located accordingly. In a corresponding embodiment, the carrier device advantageously has the form of part of a cylinder barrel, preferably of half of a cylinder barrel (or a curved plane, respectively). An opening angle of about 90° and/or no more than about 90° for such a part of a cylinder barrel is possible to still ensure simultaneous detection of all the markers relevant for location and/or identification. If the markers are distributed over a surface of the cylinder barrel which covers no more than the mentioned opening angle, the deepest shadow will suffice for detection. The more markers are used or the more complex the characteristic pattern of the marker foil device is, the higher the probability will be for automatic detection (without re-registration) despite a position change after registration.

A system comprising the reference foil and the carrier device and advantageously a holding part as described above also is part of the invention. The dimension of the reference foil and the carrier device, i.e. of a corresponding system, may be in a two-dimensional projection about 10 cm×10 cm or about 100 cm² or have a lateral extension of no less than about 5 or 7 cm and no more than about 13 or 15 cm, thus having a surface area of no less than about 25 cm² and no more than about 225 cm². It is possible for objects (for example, instruments and/or parts of a body) to which the system and/or the reference foil is attached to be identified and/or differentiated from each other by detection.

The reference foil is suitable for use in a surgical navigation method especially within the framework of image-guided surgery. To this end, it may be part of a navigation system. A navigation system and/or surgical navigation system is understood to mean a system consisting of: at least one marker foil device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) comprises in particular a processor (CPU), a working memory, advantageously an indicating device (for example, a visual indicating device such as a monitor and/or an audio indicating device such as a loudspeaker) and advantageously a permanent data memory, wherein the data processing device processes navigation data forwarded to it by the receiver and can advantageously output guidance information to a user via the indicating device. Preferably, the navigation data can be stored in the permanent data memory and for example compared with data which have been stored in said memory beforehand.

As another part of the invention, a method for producing the above-mentioned reference foil is described. In order to have a known and well-defined geometric relationship between the marker foil device and the carrier device, it is necessary to have precise knowledge of the position of the marker foil device with respect to the attaching part. When producing the reference foil, it thus is of great advantage not to move the support foil between fixing of the at least one marker foil device to the support foil and forming of the attaching part, i.e. the support foil is kept stationary when the step of fixing and forming is performed, in particular until the last of the two steps (i.e. both steps) is completed. In particular, the step of fixing and the step of forming is performed simultaneously, in order to assure that the support foil is stationary during the process. Preferably, an attaching part is formed by punching out or cutting out a part of the support foil. If a machine for producing the reference foil is designed such that it can fix (i.e. preferably glue) the markers to the support foil simultaneously to forming the attaching part on the reference foil while the support foil is held in a known and fixed position by the machine, a known geometry and/or relative position between the attaching part and the marker foil device and thus also between the marker foil device and the object (the position of the latter being designated by the position of the reference foil) is ensured.

As further steps of the method, an adhesive (i.e. a glue) may be supplied onto the support foil at locations at which the marker foil device is to be placed onto the support foil. Alternatively or additionally, an adhesive may be placed on the side of a marker material foil which shall later on (when formed into a marker) be placed onto the support foil. A marker material foil out of which the marker or markers are to be formed and the support foil may then be attached to each other (e.g. by gluing). A marker foil device may be mechanically separated (e.g. by punching and/or cutting) from the bulk of the marker material foil without damaging the supporting foil. Damage-free punching may be achieved by adjustment of an appropriate punching depth. Thus, the marker foil device is formed on or attached to, respectively, the supporting foil simultaneously to forming the attaching part. The slug (i.e. the unused or unusable remainder) of the marker material foil may then be removed from the marker foil device and the supporting foil for later use or disposal, respectively.

In another embodiment of the method, support material foil (out of which the support foil is to be formed) may be attached (e.g. by using an adhesive, i.e. gluing) to the marker material foil. Then a template with openings at locations at which the markers (pieces of marker material foil) are designed to be is punched and/or cut into the support material foil without damaging the marker material foil, thereby leaving visual access to parts of the marker material foil which then constitute the markers. Those parts are preferably not covered by adhesive during the process. The punching and/or cutting is preferably done simultaneously to forming the attaching part into the support material foil and advantageously also into the marker material foil. The two material foils in this case have preferably the same dimensions as blanks and thus one foil underlies the other completely during the punching and/or cutting process, the attaching part thus having to be formed into both foils. The slug (i.e. the unused or unusable remainder) of the support material foil may then be disposed of.

In the following, a preferred embodiment of the invention is described in conjunction with the appended figures.

Figure 1:
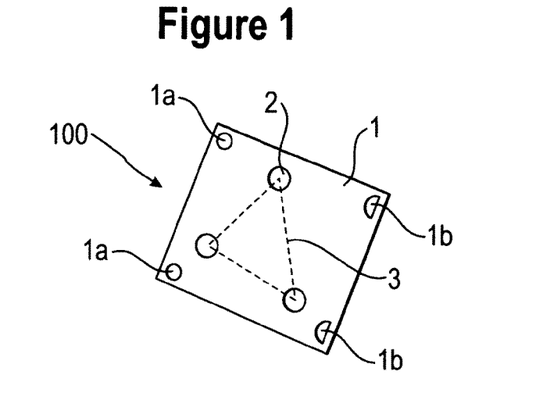
FIG. 1 shows a reference foil.

FIG. 1 displays a reference foil 100 comprising a carrier surface, in particular a carrier substrate 1 made of a thin film of Mylar™. A passive marker foil device comprising marker elements, in particular marker labels 2 having a circular geometry, is attached to the carrier substrate 1. The marker labels 2 are pieces of a marker material foil (e.g. a retroreflecting foil). The marker labels 2 are made of a retroreflecting foil with an adhesive side, in particular an adhesive back side which may be stuck onto and/or attached to the carrier substrate 1. The positions of the three marker labels 2 are chosen such that when the carrier substrate 1 is laid flat, the positions of the marker labels (in particular, their circular centres) mark the corners of a triangle 3, advantageously a non-symmetric or non-equilateral and non-isosceles triangle, respectively. Thus, advantageously no two sides of that triangle 3 have equal length. It may be envisaged within the framework of this invention that along the dotted lines in FIG. 1 which mark triangle 3, additional marker elements, in particular elongated and/or linear marker elements are attached to the carrier substrate 1 such that the marker labels 2 are connected with one another. Additionally, a coloured thin film may be used for the carrier substrate 1 so that visual recognition of reference foils 100 with different geometries of marker foil devices is supported.

The reference foil 100 further comprises attaching parts formed by fixing portions 1a, 1b for fixing the carrier substrate 1 to a carrier device such as a frame 400 which is discussed below. The fixing portions 1a, 1b advantageously take the form of cut-outs or punch-outs, in this case semicircular punch-outs on one side, preferably in two adjacent corners of the carrier substrate 1. The fixing portions 1a, 1b may also serve as alignment portions for aligning the carrier substrate 1 with the frame 400.

Figure 2:
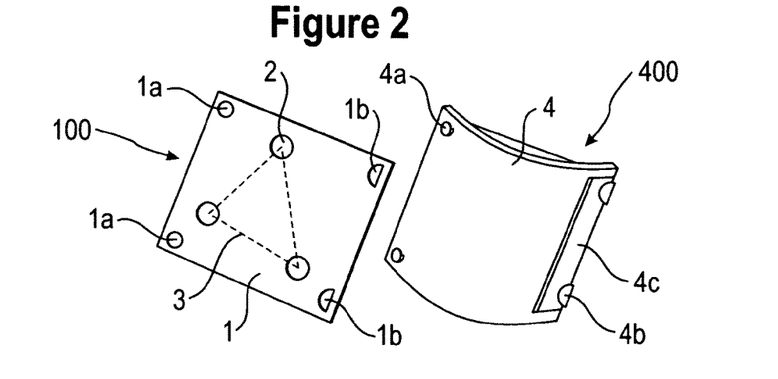
FIG. 2 shows a reference foil and a convex-shaped frame.

FIG. 2 shows a reference foil 100 and a carrier device comprising a frame 400 for carrying the reference foil 100. The frame 400 comprises a carrying surface 4 which is preferably convex towards the side to which the reference foil 100 is attached. Furthermore, the frame 400 is provided with fixing parts 4a formed as at least partly cylindrical prominent features on the surface of the carrying surface 4. The fixing parts 4a, 4b are designed to fit around fixing portions 1a, 1b of the reference foil 100 which may be formed as cut-outs or punch-outs, in this case circular cut-outs or punch-outs of the carrier substrate 1. Preferably, the fixing parts 4a, 4b form a negative to the geometry of the fixing portions 1a, 1b such that both fit together in a stable mechanical connection supported by a form fit.

The carrying surface 4 advantageously is a free-formed component and does not only provide increased flexural stiffness but is also very effective to prevent gaps between the carrier substrate 1 and the frame; due to the convex shape of the carrying surface 4, any movement of the reference foil 100 would lead to tensile load in the carrier substrate 1 and not a bending load. As the carrier substrate 1 provides good tensile strength and stiffness (preferably a tensile strength which is larger than about 100 N/mm$^2$, more preferably much larger than 100 N/mm$^2$, in particular a tensile strength of 500 N/mm$^2$ or 1000 N/mm$^2$ and/or in an interval with a lower boundary of 500 N/mm$^2$ and/or an upper boundary of 1000 N/mm$^2$), no unwanted movement is expected as soon as the carrier substrate 1 is fixed to both sides of the convex shaped carrying surface 4. Preferably, the carrier substrate 1 is slid over the fixing parts 4a before being formed onto the carrying surface 4 and being aligned with the frame 400 by locating it on the fixing parts 4b which are part of the tensioning part 4c and are preferably located on the side of the carrying surface 4 to which the reference foil 100 is attached. Alternatively, the fixing parts 4b may be located on the side of the carrying surface 4 which is averse to the reference foil 100 when the latter is attached to the frame 400 (that side may in the following also be referred to a back side, the side of the carrying surface 4 facing the reference foil 100 being called a front side). In that case, the carrier substrate 1 may overlap (in particular, be wound around) at least one edge of the carrying surface 4 so that additional stability of the reference foil 100 on the frame 400 is provided by applying an additional holding force. Preferably, the fixing parts 4a, 4b take the form of prominent features which form a negative to the fixing portions 1a, 1b such that both fit together in a stable mechanical connection supported by a form fit. The fixing parts 4a, 4b may take the function of the alignment parts which have been described above. In particular those fixing parts over which the reference foil 100 is located last, in this case fixing parts 4b, may serve this purpose. Fixing parts 4b are therefore located on preferably a side of the carrying surface 4 which is opposite to the side on which fixing parts 4a over which the reference foil 100 is located first. The fixing parts 4b may located on and/or be part of a tensioning part 4c for tensioning the reference foil after it has been attached to the frame 400. The tensioning part may comprise a snap hook which may be part of or identical with fixing parts 4b. The snap hook is designed to grip the reference foil 100 and/or to engage at least partly into fixing portions 1b such that is held in place e.g. during tensioning. The tensioning part 4c advantageously comprises a double plate which slides over a portion of the carrying surface 4 and may comprise a spring mechanism which keeps the tensioning part 4c in a loaded state when it is moved in a direction away from the centre of carrying surface 4. In a certain embodiment, the tensioning part 4c may also comprise a guide part which is preferably located on the side of the tensioning part 4c facing the back side of the carrying surface 4. The guide part may take the form of a prominent feature which functions as a handhold or a handle, respectively, for manually moving the tensioning part 4c. This avoids having to touch and thus possibly soiling the front side of the system of reference foil 100 and frame 400 when tensioning the reference foil 100 on the frame 400.

Figure 3:
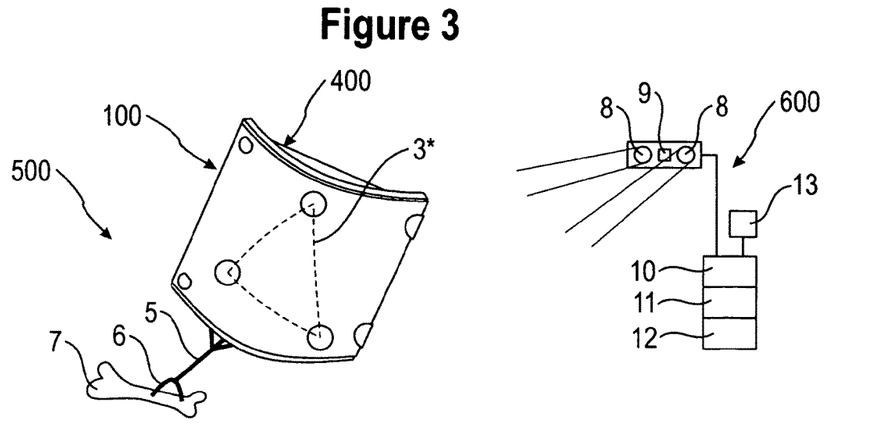
FIG. 3 shows a reference foil when attached to a frame.

FIG. 3 shows a system of the reference foil 100 attached to the frame 400, which is connected to a marker holder 5 with a holder fixture 6. Such a system may also be referred to as a reference foil array 500. The reference foil array 500 is fixed by the holder fixture 6 to a body part, in this case a bone structure 7. The marker holder 5 is mechanically stably connected to the frame 400. All parts of the reference foil array 500 may be comprise and/or made of radiolucent material such as polycarbonates or plastics, respectively. It is to be noted that compared to the situation in FIGS. 1 and 2, the three-dimensional geometry of the marker foil device is deformed if the reference foil 100 is attached to the frame 400. The original triangle 3 (in its undeformed geometry which was completely located in a plane) is now spun around a convex surface defined by the carrying surface 4, whereby the third dimension coordinate of the marker foil device is no longer constant compared to triangle 3. Thus, the triangle 3 is given a deformed geometry 3*. There is a simple mathematical relation between the undeformed geometry (3) and the deformed one (3*) which may be described by a linear transformation or a projection, respectively, from a plane into the curved or convex geometry of the carrying surface 4. Preferably, the marker foil device is unsymmetric at least if it is deformed.

FIG. 3 further display a navigation system 600 comprising a stereotactic camera 8, an electromagnetic emitter 9 (which in particular emits infrared radiation), a processor (CPU) 10, a main memory (RAM) 10, a permanent memory 12 (such as a hard disk) and display unit such as a monitor 13. The navigation system 600 knows the deformed geometry 3*, i.e. it is provided with data which characterises the deformed geometry 3* such that the reference foil array 500 may be recognized and/or identified by the navigation system 600. Such a recognition and/or identification may be performed by the processor 10 which may to this end compare the data relating to the known geometry of the reference foil array 500 to data taken by the navigation system 600 relating to the actual geometry of the reference foil array 500. The data relating to the known geometry may be saved on permanent memory 12 and read from there by the processor 10. The actual geometry of the reference foil array 500 may be determined by measuring the position of the marker labels 2 and thereby calculating the geometry of a surface in which all three positions may be and/or in fact are located. In a two-dimensional projection of the measured positions of marker labels 2 (i.e. of their three-dimensional coordinates) into the viewing plane of the stereotactic camera 8, the geometry outlined by these coordinates depends on the perspective, i.e. the angle of view from the stereotactic camera onto e.g. the parts of the reference foil 100 or the carrying surface 4, respectively, on to which the marker labels 2 are attached. It may be possible that out the plurality of three marker labels 2, only two are visible to the stereotactic camera 8 from a certain perspective. Thus, at least the geometry, in particular characteristic geometry of two such marker labels 2 (i.e. of at least a part, in particular a characteristic part of the marker foil device) must be known to the navigation system 600. Such a characteristic geometry may for example be the distance between two marker labels 2 and/or an angle between two linear features of retroreflecting foil.

Figure 4A:
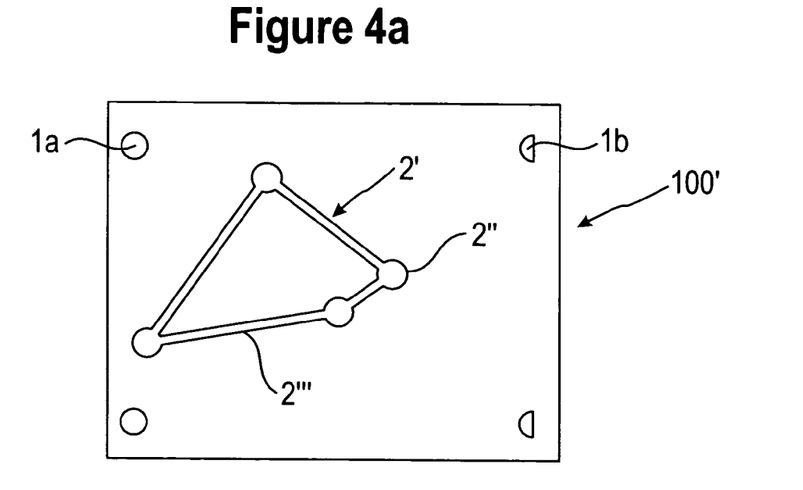
FIGS. 4a and 4b show a reference foil with an integral marker foil device.

FIG. 4a displays a reference foil 100' according to a further embodiment with an integral marker foil device 2'. The integral marker foil device 2' comprises an unsymmetric pattern of marker labels 2" which are contiguously connected by bridges 2''' which are preferably also made of marker material foil. At least the outline, in particular the outer boundary of the integral marker foil device 2' lacks any symmetry or periodically recurring geometric features. In particular, the rounded-off corners of the polygonal layout formed by the marker labels 2" have different distances to each other corner.

Figure 4B:
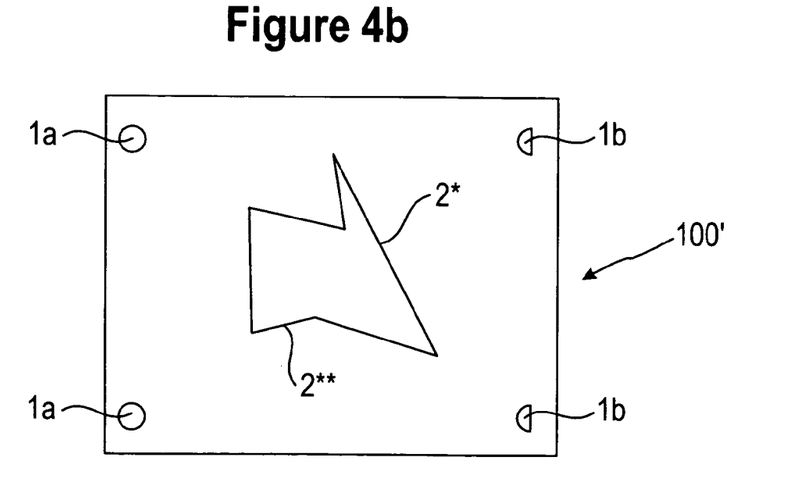

FIG. 4b shows an alternative to the integral marker foil device 2' of FIG. 4a. In this embodiment, the integral marker foil device is formed by a single marker label 2* which is constituted by a patch with an unsymmetric and non-periodic boundary, in particular periphery 2**.

The invention claimed is:

1. A method of tracking a patient's body part or an instrument via a reference foil array, the reference foil array including a reference foil having a carrier surface and a plurality of openings in the carrier surface serving as attaching parts, a marker foil device that does not display any symmetry when viewed by a navigation system and that reflects or emits electromagnetic radiation and has a surface that is fixedly attached to the carrier surface, a carrier device having an inflexible curved carrier surface and a plurality of fixing parts extending outwardly from the curved carrier surface, and a marker holder having a first end connected to the carrier device and a second end having a holding fixture, the method comprising:

engaging each of the plurality of fixing parts with one of the openings in the carrier surface to detachably secure the reference foil to the carrier device in a fixed position;

attaching the second end of the marker holder to the patient's body part or the instrument; and tracking the spatial position of the patient's body part or the instrument by recognizing and/or identifying the marker foil device using the navigation system that includes a camera and an electromagnetic emitter.

2. The method according to claim 1, wherein the marker foil device includes a plurality of marker labels.

3. The method according to claim 2, wherein the plurality of marker labels are contiguously connected by bridges.

4. The method according to claim 2, wherein the plurality of marker labels are positioned on the reference foil to mark corners of a triangle.

5. The method according to claim 4, wherein the triangle is a non-symmetric or non-equilateral and non-isosceles triangle.

6. The method according to claim 1, wherein the reference foil is substantially rectangular, and wherein one of the plurality of attaching parts is provided near each corner of the reference foil.

7. The method according to claim 1, wherein the curved carrier surface is convex.

8. The method according to claim 1, wherein the plurality of fixing parts extend outwardly from the curved carrier surface on a carrying side to which the reference foil is attached in a direction substantially perpendicular to the curved carrier surface.

9. The method according to claim 1, wherein tracking includes comparing a known geometry of the reference foil array to data taken by the navigation system relating to an actual geometry of the reference foil array.

10. The method according to claim 9, wherein the marker foil device includes a plurality of marker labels, and wherein the actual geometry is determined by measuring a position of at least two of the plurality of marker labels and calculating a geometry of the carrier surface.

11. A method of tracking a patient's body part or an instrument, the method including:

providing a reference foil having carrier surface with a plurality of openings and a marker foil device that does not display any symmetry when viewed by a navigation system and having a surface that is fixedly attached to the carrier surface of the reference foil for reflecting or emitting electromagnetic radiation;

providing a carrier device with an inflexible curved carrier surface and a plurality of fixing parts extending outwardly from the inflexible curved carrier surface;

providing a marker holder having a first end connected to the carrier device;

securing the reference foil to the inflexible carrier device in a fixed position, including engaging each of the plurality of fixing parts with one of the openings in the carrier surface to detachably secure the reference foil to the carrier device in the fixed position;

attaching a second end of the marker holder to the patient's body part or the instrument; and tracking the spatial position of the patient's body part or the instrument by recognizing and/or identifying the marker foil device using the navigation system.

12. The method according to claim 11, wherein providing the marker foil device further includes providing a plurality of marker labels.

13. The method according to claim 12, wherein providing the plurality of marker labels includes providing the plurality of marker labels in a position on the reference foil to mark corners of a triangle.

14. The method according to claim 11, wherein tracking includes comparing a known geometry of the reference foil to data taken by the navigation system relating to an actual geometry of the reference foil.

15. The method according to claim 14, wherein the marker foil device includes a plurality of marker labels, and wherein the actual geometry is determined by measuring a position of at least two of the plurality of marker labels and calculating a geometry of the carrier surface.

16. A method of tracking a patient's body part or an instrument, the method including:
   providing a reference foil having carrier surface and a plurality of openings in the carrier surface serving as attaching parts;
   providing a marker foil device that does not display any symmetry when viewed by a navigation system and having a surface that is fixedly attached to the carrier surface of the reference foil for reflecting or emitting electromagnetic radiation;
   providing a carrier device having an inflexible curved carrier surface and a plurality of fixing parts extending outwardly from the curved carrier surface;
   providing a marker holder having a first end connected to the carrier device;
   engaging each of the plurality of fixing parts with one of the openings in the carrier surface to detachably secure the reference foil to the carrier device in a fixed position;
   attaching a second end of the marker holder to the patient's body part or the instrument; and
   tracking the spatial position of the patient's body part or the instrument by recognizing and/or identifying the marker foil device using the navigation system.

17. The method according to claim 16, wherein providing the carrier device further includes providing the fixing parts as part of a tensioning part that slides over a portion of the carrying surface and is in a loaded state when moved away from a center of the carrying surface.

* * * * *